United States Patent
Faig et al.

(10) Patent No.: US 11,129,789 B2
(45) Date of Patent: Sep. 28, 2021

(54) STABILIZED COSMETIC COMPOSITIONS

(71) Applicant: L'OREAL, Paris (FR)

(72) Inventors: Jonathan James Faig, Sayreville, NJ (US); David Chan, Edison, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/169,286

(22) Filed: Oct. 24, 2018

(65) Prior Publication Data

US 2020/0129417 A1    Apr. 30, 2020

(51) Int. Cl.
| | |
|---|---|
| *A61K 8/60* | (2006.01) |
| *A61K 8/9789* | (2017.01) |
| *A61K 8/26* | (2006.01) |
| *A61Q 17/04* | (2006.01) |
| *A61Q 19/00* | (2006.01) |

(52) U.S. Cl.
CPC ............ *A61K 8/9789* (2017.08); *A61K 8/602* (2013.01); *A61Q 17/04* (2013.01); *A61K 2800/432* (2013.01); *A61K 2800/52* (2013.01); *A61K 2800/522* (2013.01)

(58) Field of Classification Search
CPC .. A61K 8/9789; A61K 8/602; A61K 2800/52; A61K 2800/432; A61K 2800/522; A61Q 17/04; A61Q 19/00
See application file for complete search history.

(56) References Cited

U.S. PATENT DOCUMENTS

| | | | |
|---|---|---|---|
| 3,673,146 A | 6/1972 | Factor | |
| 2005/0244349 A1* | 11/2005 | Chaudhuri | A61K 8/37 424/59 |
| 2006/0018858 A1* | 1/2006 | Chen | A61K 8/498 424/70.13 |
| 2010/0272833 A1* | 10/2010 | McClellan | A61K 31/565 424/727 |
| 2014/0134120 A1* | 5/2014 | Jouy | A61K 8/4966 424/59 |
| 2017/0369611 A1* | 12/2017 | Huang | C08F 210/16 |

OTHER PUBLICATIONS

Chemical Book, Pigment Blue 29 data sheet, obtained online Jan. 12, 2021.*

* cited by examiner

*Primary Examiner* — Mina Haghighatian

(74) *Attorney, Agent, or Firm* — McNees Wallace & Nurick LLC

(57) ABSTRACT

A cosmetic composition includes a non-acid-resistant-grade ultramarine dye, a stabilizing agent, at least one additive, and water. The ultramarine dye may be present at a concentration of about 0.1% to about 0.4%, by weight, of the cosmetic composition and may include a trisulfur radical anion. The stabilizing agent may include baicalin and may be at a concentration of about 0.2% or less, by weight, of the cosmetic composition. The cosmetic composition may have a pH in the range of 6.5 to 8.0. A method of stabilizing a cosmetic composition includes forming a cosmetic composition including a non-acid-resistant-grade ultramarine dye, a stabilizing agent, at least one additive, and water. The method also includes adjusting a pH of the cosmetic composition to a predetermined value. The stabilizing agent inhibits degradation of the ultramarine dye, thereby stabilizing the cosmetic composition and inhibiting generation of an odor caused by degradation of the ultramarine dye.

21 Claims, No Drawings

STABILIZED COSMETIC COMPOSITIONS

FIELD OF THE INVENTION

The invention relates to cosmetic compositions with improved stability against degradation. More specifically, the invention relates to cosmetic compositions including a non-acid-resistant-grade ultramarine and a stabilizing agent.

BACKGROUND OF THE INVENTION

Topical formulations, such as, for example, cosmetic compositions, for keratinous substrates, such as, for example, skin or hair, may include pigments as ingredients. Pigments may be used to provide color, luster, sparkle, or other properties to the topical formulations. Certain pigments may be unstable under certain conditions, such as, for example, a particular pH condition or a particular temperature condition, in such topical formulations, with the degradation of the pigment having a negative effect on the topical formulation, such as, for example, changing the color of the topical formulation or causing the topical formulation to have an objectionable odor.

There is a need for a formulation that overcomes one or more of the aforementioned drawbacks associated with products that employ one or more unstable pigments in the composition by improving the stability of the unstable pigment in the composition. Such a formulation would provide a product that retains its original characteristics over a longer period of time.

BRIEF SUMMARY OF THE INVENTION

The summary is provided to introduce a selection of concepts in a simplified form that are further described below in the detailed description of the invention. This summary is not intended to identify key features of the claimed subject matter, nor is it intended to be used as an aid in determining the scope of the claimed subject matter.

The compositions hereof are characterized, in various embodiments, as including a non-acid-resistant-grade ultramarine dye, a stabilizing agent, at least one additive, and water.

In some embodiments, the non-acid-resistant-grade ultramarine dye is at a concentration of about 0.1% to about 0.4%, by weight, of the cosmetic composition.

In some embodiments, the non-acid-resistant-grade ultramarine dye includes a trisulfur radical anion.

In some embodiments, the stabilizing agent includes baicalin at a concentration of about 0.2% or less, by weight, of the cosmetic composition.

In some embodiments, the cosmetic composition has a pH in the range of 6.5 to 8.0.

In some embodiments, the stabilizing agent stabilizes the non-acid-resistant-grade ultramarine dye against degradation.

The methods hereof are characterized, in various embodiments, as including forming a cosmetic composition and adjusting a pH of the cosmetic composition to a predetermined value. The formed cosmetic composition includes a non-acid-resistant-grade ultramarine dye, a stabilizing agent, at least one additive, and water. The stabilizing agent inhibits degradation of the non-acid-resistant-grade ultramarine dye, thereby stabilizing the cosmetic composition and inhibiting generation of an odor caused by degradation of the non-acid-resistant-grade ultramarine dye.

Other features and advantages of the present invention will be apparent from the following more detailed description, by way of example, the principles of the invention.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

DETAILED DESCRIPTION OF THE INVENTION

According to the disclosure, a cosmetic composition is provided that includes a stabilizing agent and a non-acid-resistant-grade ultramarine dye stabilized by the stabilizing agent.

The stabilizing agent provides the surprising and unexpected benefit of reducing or eliminating an undesirable odor that may be associated with the cosmetic composition in a pH range of about 6.5 to about 8. In exemplary embodiments, the benefit results from a reduction or elimination of the rate or amount of degradation of the non-acid-resistant-grade ultramarine dye based on the presence of the stabilizing agent and relative to the same or substantially similar composition conditions in the absence of the stabilizing agent.

The cosmetic composition may be any water-based cosmetic composition with a measurable pH. Appropriate types of cosmetic composition may include, but are not limited to, moisturizers, sunscreens, water-based makeup products, hair dyes, shampoos, and conditioners.

Non-Acid-Resistant-Grade Ultramarine Dyes

In accordance with the disclosure, provided are cosmetic compositions that include at least one non-acid-resistant-grade ultramarine dye. In some embodiments, the non-acid-resistant-grade ultramarine dye serves as a pigment to affect the color of the cosmetic composition. In some embodiments, the ultramarine dye provides color correction to the cosmetic composition. In accordance with the various embodiments, the non-acid-resistant-grade ultramarine dye is a commercially-available composition. In exemplary embodiments, the non-acid-resistant-grade ultramarine dye is an unstable pigment in an aqueous environment at a predetermined pH of the composition in the absence of a stabilizing agent. In exemplary embodiments, the non-acid-resistant-grade ultramarine dye includes a trisulfur radical anion. In exemplary embodiments, the non-acid-resistant-grade ultramarine dye generates a sulfur odor upon degradation of the trisulfur radical anion.

More particularly, the non-acid-resistant-grade ultramarine dye is present in the composition at a concentration, by weight, based on the total weight of the composition, of about 0.4% or less, alternatively from about 0.1% to about 0.4%, alternatively from about 0.1% to about 0.3%, alternatively from about 0.15% to about 0.25%, alternatively about 0.1%, alternatively about 0.2%, alternatively about 0.3%, alternatively about 0.4%, or any suitable value, range, or sub-range thereof, by weight, based on the weight of the composition.

Stabilizing Agents

In accordance with the disclosure, provided are cosmetic compositions that further include at least one stabilizing agent. The stabilizing agent inhibits or prevents degradation of the non-acid-resistant-grade ultramarine dye in an aqueous environment at a predetermined pH of the composition, thereby inhibiting or preventing an odor generation upon degradation of the non-acid-resistant-grade ultramarine dye. In some embodiments, the stabilizing agent includes at least one antioxidant.

In some embodiments, the at least one antioxidant includes a flavone glycoside, a hydrophilic-modified flavonol, an isoflavonoid, or combinations thereof. Appropriate flavone glycosides may include, but are not limited to, baicalin, quercetin, kaempferol, and isorhamnetin. In exemplary embodiments, the flavone glycoside includes baicalin. In exemplary embodiments, the stabilizing agent is provided in a *Scutellaria Baicalensis* root extract. In exemplary embodiments, the *Scutellaria Baicalensis* root extract is at least 95% baicalin, by weight. The stabilizing agent is preferably provided in an amount sufficient to inhibit or prevent degradation of the non-acid-resistant-grade ultramarine dye in an aqueous environment at a predetermined pH of the composition.

More particularly, the stabilizing agent is present in the composition at a concentration, by weight, based on the total weight of the composition, of about 0.4% or less, alternatively from about 0.1% to about 0.4%, alternatively from about 0.1% to about 0.3%, alternatively from about 0.15% to about 0.25%, alternatively about 0.1%, alternatively about 0.2%, alternatively about 0.3%, alternatively about 0.4%, or any suitable value, range, or sub-range thereof, by weight, based on the weight of the composition.

Additives

In accordance with the disclosure, the composition further includes at least one additive. The at least one additive may be selected to provide a cosmetic composition of a predetermined type having at least one predetermined property. The total amount of the at least one additive may be any appropriate amount, such as, for example, about 50% or less, alternatively from about 40% to about 50%, alternatively from about 30% to about 50%, alternatively about 60% or less, alternatively from about 40% to about 60%, or any suitable value, range, or sub-range thereof, by weight, based on the weight of the composition.

The at least one additive may include, but is not limited to, at least one polymer, at least one non-ultramarine cosmetic colorant, at least one active, at least one preservative, at least one non-water solvent, at least one sun filter, at least one pearl pigment, at least one surfactant, at least one fatty compound, at least one vitamin, at least one adjuvant, or combinations thereof.

The cosmetic composition may include any number of appropriate polymers as additives. Appropriate polymers for the cosmetic composition may include, but are not limited to, methyl methacrylate crosspolymer, ammonium polyacryloyldimethyl taurate, xanthan gum, or combinations thereof. The total amount of the polymers may be any appropriate amount, such as, for example, about 5% or less, alternatively from about 2.5% to about 5%, by weight, based on the weight of the composition.

The cosmetic composition may include any number of appropriate non-ultramarine cosmetic colorants approved for use in food, drug, and cosmetics by the Food and Drug Administration (FDA) as additives. Appropriate non-ultramarine cosmetic colorants for the cosmetic composition may include, but are not limited to, blue 1, blue 2, green 3, red 3, red 40, yellow 5, yellow 6, citrus red 2, orange B, violet 2, or combinations thereof. The total amount of the non-ultramarine dyes may be any appropriate amount, such as, for example, about 0.1% or less, alternatively from about 0.05% to about 0.1%, by weight, based on the weight of the composition.

The cosmetic composition may include any number of appropriate actives as additives. Appropriate actives for the cosmetic composition may include, but are not limited to, phenylethyl resorcinol, hydroxyethyl urea, caffeine, hydroxyethylpiperazine ethane sulfonic acid, capryloyl salicylic acid, sodium hyaluronate, retinol, ascorbyl tetraisopalmitate, ascorbyl glucoside, or combinations thereof. The total amount of the actives may be any appropriate amount, such as, for example, about 5% or less, alternatively from about 2.5% to about 5%, by weight, based on the weight of the composition.

The cosmetic composition may include any number of appropriate preservatives as additives. Appropriate preservatives for the cosmetic composition may include, but are not limited to, chlorphenesin, phenoxyethanol, or combinations thereof. The total amount of the preservatives may be any appropriate amount, such as, for example, about 1% or less, alternatively from about 0.5% to about 1%, by weight, based on the weight of the composition.

The cosmetic composition may include any number of appropriate non-water solvents as additives. Appropriate non-water solvents for the cosmetic composition may include, but are not limited to, caprylyl glycol, glycerin, C12-15 alkyl benzoate, or combinations thereof. The total amount of the non-water solvents may be any appropriate amount, such as, for example, about 20% or less, alternatively from about 10% to about 20%, by weight, based on the weight of the composition.

The cosmetic composition may include any number of appropriate sun filter as additives. Appropriate sun filters for the cosmetic composition may include, but are not limited to, homosalate, ethylhexyl salicylate, octocrylene, butyl methoxydibenzoylmethane, or combinations thereof. The total amount of the sun filters may be any appropriate amount, such as, for example, about 20% or less, alternatively from about 10% to about 20%, by weight, based on the weight of the composition.

The cosmetic composition may include any number of appropriate pearl pigments as additives. Appropriate pearl pigments for the cosmetic composition may include, but are not limited to, mica, synthetic fluorphlogopite, titanium dioxide, tin dioxide, or combinations thereof. The total amount of the pearl pigments may be any appropriate amount, such as, for example, about 2% or less, alternatively from about 1% to about 2%, by weight, based on the weight of the composition.

The cosmetic composition may include any number of appropriate surfactants as additives. Appropriate surfactants for the cosmetic composition may include, but are not limited to, glyceryl stearate, myristic acid, palmitic acid, stearic acid, PEG-100 stearate, seareth-100, or combinations thereof. The total amount of the surfactants may be any appropriate amount, such as, for example, about 8% or less, alternatively from about 4% to about 8%, by weight, based on the weight of the composition.

The cosmetic composition may include any number of appropriate fatty compounds as additives. Appropriate fatty compounds for the cosmetic composition may include, but are not limited to, octyldodecanol, coconut oil, or combinations thereof. The total amount of the fatty compounds may be any appropriate amount, such as, for example, about 6% or less, alternatively from about 3% to about 6%, by weight, based on the weight of the composition.

The cosmetic composition may include any number of appropriate vitamins as additives. Appropriate vitamins for the cosmetic composition may include, but are not limited to, niacinamide. The total amount of the vitamins may be any appropriate amount, such as, for example, about 1% or less, alternatively from about 0.5% to about 1%, by weight, based on the weight of the composition.

The cosmetic composition may include any number of other appropriate additives or adjuvants. Representative additives and adjuvants include, for example, water-soluble or water-miscible solvents or co-solvents, dispersion enhancing agents, moisturizers, colorants, fillers, antioxidants (e.g., ethylenediaminetetraacetic acid (EDTA), butylated hydroxytoluene (BHT), and tocopherol), essential oils, fragrances, dyes, neutralizing or pH-adjusting agents (e.g., citric acid, triethylamine (TEA), and sodium hydroxide), conditioning or softening agents (e.g., panthenol and allantoinin) and extracts, such as botanical extracts. Additives and adjuvants may be present in the compositions in amounts generally ranging from about 0.01% to about 10% by weight. Examples of cosmetic active agents or dermatological active agents include sunscreen agents (e.g., inorganic sunscreen agent, such as titanium dioxide and zinc oxide and organic sunscreen agents, such as octocrylene, ethylhexyl methoxycinnamate, and avobenzone), free-radical scavengers, keratolytic agents, vitamins (e.g., Vitamin E and derivatives thereof), anti-elastase and anti-collagenase agents, peptides, fatty acid derivatives, steroids, trace elements, extracts of algae and of planktons, enzymes and coenzymes, flavonoids and ceramides, hydroxy acids and mixtures thereof, and enhancing agents.

Water

In accordance with the disclosure, the composition is a water-based composition having a measurable pH.

In accordance with the various embodiments, water is present in the composition at a concentration, by weight, based on the total weight of the composition, of about 40% or greater, alternatively about 70% or less, alternatively from about 40% to about 70%, alternatively from about 40% to about 60%, alternatively from about 45% to about 60%, alternatively from about 45% to about 55%, alternatively from about 45% to about 50%, alternatively from about 50% to about 60%, alternatively from about 50% to about 55%, alternatively from about 55% to about 60%, alternatively about 50%, 51%, 52%, 53%, 54%, 55%, 56%, 57%, 58%, 59%, 60%, or any suitable value, range, or sub-range thereof, by weight, based on the weight of the composition.

Raw Materials

Compositions as described in the representative embodiments according to the disclosure, and compositions as exemplified herein include raw materials selected from commercially available materials.

EXAMPLES

The invention is further described in the context of the following examples, which are presented by way of illustration, not of limitation. The inventive compositions may be used, for example, as a commercial daily sun protection factor (SPF) product or as a base composition for such a commercial cosmetic product.

Compositions

Two comparative compositions were formed that included a non-acid-resistant-grade ultramarine dye ("ultramarines") but lacked a stabilizing compound. TABLE 1 lists the ingredients and their amounts in weight percentage in Comparative Example 1 and Comparative Example 2.

TABLE 1

Comparative Compositions

| PHASE | INGREDIENT | COMPARATIVE 1 | COMPARATIVE 2 |
|---|---|---|---|
| A | C12-15 ALKYL BENZOATE | 4 | 4 |
| A | CAPRYLOYL SALICYLIC ACID | 0.15 | 0.15 |
| A | COCOS NUCIFERA (COCONUT) OIL | 2 | 2 |
| A | GLYCERYL STEARATE | 1.5 | 1.5 |
| A | MYRISTIC ACID | 0.045 | 0.045 |
| A | NIACINAMIDE | 0.92 | 0.92 |
| A | SUN FILTERS | 15 | 15 |
| A | OCTYLDODECANOL | 2 | 2 |
| A | PALMITIC ACID | 0.66 | 0.66 |
| A | PEG-100 STEARATE | 1.5 | 1.5 |
| A | STEARETH-100 | 0.4 | 0.4 |
| A | STEARIC ACID | 0.795 | 0.795 |
| A | VIOLET 2 | 0.0025 | 0.0025 |
| B | CAPRYLYL GLYCOL | 0.3 | 0.3 |
| B | CHLORPHENESIN | 0.1 | 0.1 |
| B | GLYCERIN | 10 | 10 |
| B | PHENOXYETHANOL | 0.7 | 0.7 |
| B | ACTIVES | 3.773 | 3.773 |
| C | WATER | 51.5025 | 51.5025 |
| D | AMMONIUM POLYACRYLOYLDIMETHYL TAURATE | 1 | 1 |
| D | XANTHAN GUM | 0.25 | 0.25 |
| E | METHYL METHACRYLATE CROSSPOLYMER | 2 | 2 |
| E | MICA | 0.4472 | 0.4472 |
| E | SYNTHETIC FLUORPHLOGOPITE | 0.17 | 0.17 |
| E | TIN OXIDE | 0.0025 | 0.0025 |
| E | TITANIUM DIOXIDE | 0.4903 | 0.4903 |
| F | ISOPROPYL TITANIUM TRIISOSTEARATE | 0.006 | |
| F | SILICA | 0.0376 | |
| F | TRIETHOXYSILYLETHYL POLYDIMETHYLSILOXYETHYL DIMETHICONE | 0.006 | |
| F | ULTRAMARINES | 0.1504 | 0.2 |
| G | SODIUM HYDROXIDE | 0.092 | 0.092 |

Two inventive compositions were formed that included a non-acid-resistant-grade ultramarine dye ("ultramarines") and a stabilizing compound ("*Scutellaria Baicalensis* root extract"). TABLE 2 lists the ingredients and their amounts in weight percentage in Inventive Example 1 and Inventive Example 2. The compositions of Inventive Examples 1 and 2 are substantially identical to the compositions of Comparative Examples 1 and 2, except for the addition of the stabilizing agent.

TABLE 2

Inventive Compositions

| PHASE | INGREDIENT | INVENTIVE 1 | INVENTIVE 2 |
|---|---|---|---|
| A | C12-15 ALKYL BENZOATE | 4 | 4 |
| A | CAPRYLOYL SALICYLIC ACID | 0.15 | 0.15 |
| A | COCOS NUCIFERA (COCONUT) OIL | 2 | 2 |
| A | GLYCERYL STEARATE | 1.5 | 1.5 |
| A | MYRISTIC ACID | 0.045 | 0.045 |
| A | NIACINAMIDE | 0.92 | 0.92 |
| A | SUN FILTERS | 15 | 15 |
| A | OCTYLDODECANOL | 2 | 2 |
| A | PALMITIC ACID | 0.66 | 0.66 |
| A | PEG-100 STEARATE | 1.5 | 1.5 |
| A | STEARETH-100 | 0.4 | 0.4 |

TABLE 2-continued

Inventive Compositions

| PHASE | INGREDIENT | INVENTIVE 1 | INVENTIVE 2 |
|---|---|---|---|
| A | STEARIC ACID | 0.795 | 0.795 |
| A | VIOLET 2 | 0.0025 | 0.0025 |
| B | CAPRYLYL GLYCOL | 0.3 | 0.3 |
| B | CHLORPHENESIN | 0.1 | 0.1 |
| B | GLYCERIN | 10 | 10 |
| B | PHENOXYETHANOL | 0.7 | 0.7 |
| B | *SCUTELLARIA BAICALENSIS* ROOT EXTRACT | 0.2 | 0.2 |
| B | ACTIVES | 3.773 | 3.773 |
| C | WATER | 51.3025 | 51.3025 |
| D | AMMONIUM POLYACRYLOYLDIMETHYL TAURATE | 1 | 1 |
| D | XANTHAN GUM | 0.25 | 0.25 |
| E | METHYL METHACRYLATE CROSSPOLYMER | 2 | 2 |
| E | MICA | 0.4472 | 0.4472 |
| E | SYNTHETIC FLUORPHLOGOPITE | 0.17 | 0.17 |
| E | TIN OXIDE | 0.0025 | 0.0025 |
| E | TITANIUM DIOXIDE | 0.4903 | 0.4903 |
| F | ISOPROPYL TITANIUM TRIISOSTEARATE | 0.006 | |
| F | SILICA | 0.0376 | |
| F | TRIETHOXYSILYLETHYL POLYDIMETHYLSILOXYETHYL DIMETHICONE | 0.006 | |
| F | ULTRAMARINES | 0.1504 | 0.2 |
| G | SODIUM HYDROXIDE | 0.092 | 0.092 |

Methods of Preparation

The ingredients of phase A were combined and heated to about 75° C. (about 167° F.) in a primary vessel and mixed until dissolved. The ingredients of phase B were combined and heated to about 75° C. (about 167° F.) and mixed in a secondary vessel until dissolved. The contents of the secondary vessel were added slowly to the primary vessel and swept and homogenized for about 15 minutes. The ingredient (water) of phase C was then added to the primary vessel and swept and homogenized for about 15 minutes. The primary vessel was then removed from the heat source to permit cooling to room temperature. The ingredients of phase D were then added to the primary vessel and swept and homogenized for about 10 minutes. Once the primary vessel cooled below about 40° C. (about 104° F.), phases E, F, and G were added sequentially with mixing for about 5 minutes before adding the next phase each time. After the addition of sodium hydroxide (phase G), the pH of each example formulation was tested and adjusted, if needed, to 5.8 with additional sodium hydroxide.

Testing Results

The pH of each example formulation was maintained at about 5.8 for about 5 to 10 minutes to ensure mixing and homogenization of the ultramarines before portions of each example composition were adjusted to a pH of 6.5, 7.0, 7.5 and 8.0 by addition of more sodium hydroxide. The pH range of 6.5 to 8.0 covers the range of pH values typically found in commercial water-based cosmetic compositions having a measurable pH. After the target pH values of 6.5, 7.0, 7.5 and 8.0 were reached, each sample was maintained at room temperature and was then checked after 12 to 18 hours for the development of a sulfur odor. TABLE 3 shows the result of the fragrance evaluations.

TABLE 3

Fragrance Evaluation

| pH | Comparative 1 | Comparative 2 | Inventive 1 | Inventive 2 |
|---|---|---|---|---|
| 6.5 | N/D | High sulfur | N/D | No sulfur |
| 7.0 | High sulfur | Moderate sulfur | Minimal sulfur | No sulfur |
| 7.5 | High sulfur | Minimal sulfur | No sulfur | No sulfur |
| 8.0 | No sulfur | No sulfur | No sulfur | No sulfur |

Comparative Example 1 had a high sulfur odor at pH values of 7.0 and 7.5, but Comparative Example 1 had no detected sulfur odor at a pH of 8.0. In comparison, Inventive Example 1 had a minimal sulfur odor at a pH of 7.0 and no sulfur odor at pH values of 7.5 and 8.0. Thus, the stabilizing agent significantly reduced the odor of the composition at a pH of 7.0 and substantially eliminated the odor of the composition at a pH of 7.5.

Comparative Example 2 had a high sulfur odor at a pH value of 6.5, a moderate sulfur odor at a pH value of 7.0, a minimal sulfur odor at a pH of 7.5, and no detected sulfur odor at a pH of 8.0. In comparison, Inventive Example 2 had no sulfur odor at pH values of 6.5, 7.0, 7.5, and 8.0. Thus, the stabilizing agent substantially eliminated the odor of the composition at pH values of 6.5, 7.0, and 7.5.

The articles "a" and "an," as used herein, mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used. The adjective "any" means one, some, or all indiscriminately of whatever quantity.

"One or more," as used herein, means at least one, and thus includes individual components as well as mixtures/combinations.

The transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinarily associated with the specified material(s). The term "consisting essentially of" limits the scope of a claim to the specified elements, steps or material(s) and those that do not materially affect the basic and novel characteristic(s) of the claimed invention. All materials and methods described herein that embody the present invention can, in alternate embodiments, be more specifically defined by any of the transitional terms "comprising," "consisting essentially of," and "consisting of."

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%).

All percentages and ratios are calculated by weight unless otherwise indicated. All percentages are calculated based on the total composition unless otherwise indicated. Generally, unless otherwise expressly stated herein, "weight" or "amount" as used herein with respect to the percent amount of an ingredient refers to the amount of the raw material comprising the ingredient, wherein the raw material may be described herein to comprise less than and up to 100% activity of the ingredient. Therefore, weight percent of an active in a composition is represented as the amount of raw material containing the active that is used, and may or may not reflect the final percentage of the active, wherein the final percentage of the active is dependent on the weight percent of active in the raw material.

All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints. Further, it is understood that when an amount of a component is given, it is intended to signify the amount of the active material unless otherwise specifically stated.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

While the invention has been described with reference to a preferred embodiment, it will be understood by those skilled in the art that various changes may be made, and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A cosmetic composition, comprising:
   a non-acid-resistant-grade ultramarine dye that includes a trisulfur radical anion, the non-acid-resistant-grade ultramarine dye being unstable over a pH range from 6.0 to 7.5 such that the non-acid-resistant-grade ultramarine dye releases a sulfur odor upon degeneration of the trisulfur radial anion over the pH range;
   a stabilizing agent comprising at least one antioxidant, the at least one antioxidant comprising baicalin;
   at least one additive; and
   water,
   wherein the baicalin stabilizes the non-acid-resistant-grade ultramarine dye over the pH range such that, in the cosmetic composition, the non-acid-resistant-grade ultramarine dye releases reduced sulfur odor from degeneration of the trisulfur radial anion over the pH range relative to an otherwise identical cosmetic composition lacking the stabilizing agent.

2. The cosmetic composition of claim 1, wherein the at least one additive further comprises an antioxidant that is not baicalin.

3. The cosmetic composition of claim 1, wherein the stabilizing agent comprises *Scutellaria Baicalensis* root extract, the *Scutellaria Baicalensis* root extract comprising the baicalin of the at least one antioxidant.

4. The cosmetic composition of claim 3, wherein the *Scutellaria Baicalensis* root extract is present at a concentration of about 0.2% or less, by weight, of the cosmetic composition.

5. The cosmetic composition of claim 3, wherein the baicalin constitutes, by weight, at least 95% of the *Scutellaria Baicalensis* root extract.

6. The cosmetic composition of claim 1, wherein the non-acid-resistant-grade ultramarine dye is present at a concentration of about 0.1% to about 0.4%, by weight, of the cosmetic composition.

7. The cosmetic composition of claim 1, wherein the cosmetic composition has a pH in the range of 6.5 to 8.0.

8. The cosmetic composition of claim 1, wherein the cosmetic composition is free of the sulfur odor from degeneration of the trisulfur radial anion over the pH range.

9. The cosmetic composition of claim 1, wherein the at least one additive comprises at least one active that is selected from the group consisting of phenylethyl resorcinol, hydroxyethyl urea, sodium hydroxide, disodium ethylenediaminetetraacetic acid, caffeine, hydroxyethylpiperazine ethane sulfonic acid, dipotassium phosphate, potassium phosphate, capryloyl salicylic acid, and sodium hyaluronate.

10. The cosmetic composition of claim 1, wherein the at least one additive comprises violet 2.

11. The cosmetic composition of claim 1, wherein the at least one additive comprises at least one fatty compound selected from the group consisting of octyldodecanol and *Cocos Nucifera* oil.

12. The cosmetic composition of claim 1, wherein the at least one additive comprises at least one polymer selected from the group consisting of methyl methacrylate crosspolymer, ammonium polyacryloyldimethyl taurate, and xanthan gum.

13. The cosmetic composition of claim 1, wherein the at least one additive comprises at least one pearl pigment selected from the group consisting of mica and synthetic fluorphlogopite.

14. The cosmetic composition of claim 1, wherein the at least one additive comprises at least one preservative selected from the group consisting of chlorphenesin and phenoxyethanol.

15. The cosmetic composition of claim 1, wherein the at least one additive comprises at least one solvent selected from the group consisting of caprylyl glycol, glycerin, and C12-15 alkyl benzoate.

16. The cosmetic composition of claim 1, wherein the at least one additive comprises at least one sun filter selected from the group consisting of homosalate, ethylhexyl salicylate, octocrylene, and butyl methoxydibenzoylmethane.

17. The cosmetic composition of claim 1, wherein the at least one additive comprises at least one surfactant selected from the group consisting of glyceryl stearate, myristic acid, palmitic acid, stearic acid, PEG-100 stearate, and steareth-100.

18. The cosmetic composition of claim 1, wherein the cosmetic composition is a moisturizer.

19. A cosmetic composition comprising:
   a non-acid-resistant-grade ultramarine dye at a concentration of about 0.1% to about 0.4%, by weight of the cosmetic composition, the non-acid-resistant-grade ultramarine dye including a trisulfur radical anion, the non-acid-resistant-grade ultramarine dye being unstable over a pH range from 6.0 to 7.5 such that the non-acid-resistant-grade ultramarine dye releases a sulfur odor upon degeneration of the trisulfur radial anion over the pH range;
a stabilizing agent comprising baicalin at a concentration of about 0.2% or less, by weight of the cosmetic composition;
at least one additive; and
water,
wherein the baicalin stabilizes the non-acid-resistant-grade ultramarine dye over the pH range such that, in the cosmetic composition, the non-acid-resistant-grade ultramarine dye releases reduced sulfur odor from degeneration of the trisulfur radial anion over the pH range relative to an otherwise identical cosmetic composition lacking the stabilizing agent.

20. The cosmetic composition of claim 19, wherein the cosmetic composition is free of the sulfur odor from degeneration of the trisulfur radial anion over the pH range.

21. A method of stabilizing a cosmetic composition, the method comprising:
forming a cosmetic composition comprising:
  a non-acid-resistant-grade ultramarine dye that includes a trisulfur radical anion, the non-acid-resistant-grade ultramarine dye being unstable over a pH range from 6.0 to 7.5 such that the non-acid-resistant-grade ultramarine dye releases a sulfur odor upon degeneration of the trisulfur radial anion over the pH range;
  a stabilizing agent comprising at least one antioxidant, the at least one antioxidant comprising baicalin;
  at least one additive; and
  water; and
adjusting a pH of the cosmetic composition to a predetermined value within the pH range;
wherein the baicalin stabilizes the non-acid-resistant-grade ultramarine dye over the pH range such that, in the cosmetic composition, the non-acid-resistant-grade ultramarine dye releases reduced sulfur odor from degeneration of the trisulfur radial anion over the pH range relative to an otherwise identical cosmetic composition lacking the stabilizing agent.

* * * * *